United States Patent
Ghirardello et al.

(10) Patent No.: US 9,408,932 B2
(45) Date of Patent: Aug. 9, 2016

(54) UNIT FOR STERILIZING A WEB OF PACKAGING MATERIAL FOR A MACHINE FOR PACKAGING POURABLE FOOD PRODUCTS

(75) Inventors: Roberto Ghirardello, Carpi (IT); Danilo Veroni, Rubiera (IT); Alessandro Veronesi, Limidi Di Soliera (IT); Robert Bartolini, Guiglia (IT); Daniele Apparuti, Montale Rangone (IT); Renzo Bellei, Modena (IT)

(73) Assignee: TETRA LAVAL HOLDINGS & FINANCE S.A., Pully (CH)

(*) Notice: Subject to any disclaimer, the term of this patent is extended or adjusted under 35 U.S.C. 154(b) by 113 days.

(21) Appl. No.: 14/238,399

(22) PCT Filed: Aug. 29, 2012

(86) PCT No.: PCT/EP2012/066758
§ 371 (c)(1),
(2), (4) Date: Feb. 11, 2014

(87) PCT Pub. No.: WO2013/045192
PCT Pub. Date: Apr. 4, 2013

(65) Prior Publication Data
US 2014/0199215 A1 Jul. 17, 2014

(30) Foreign Application Priority Data
Sep. 30, 2011 (EP) .................................... 11183645

(51) Int. Cl.
*A61L 2/18* (2006.01)
*B65B 55/10* (2006.01)

(52) U.S. Cl.
CPC *A61L 2/18* (2013.01); *B65B 55/103* (2013.01)

(58) Field of Classification Search
CPC ................................ A61L 2/18; B65B 55/103
See application file for complete search history.

(56) References Cited

U.S. PATENT DOCUMENTS 6,354,061 B1 * 3/2002 Bellei .................. B65B 55/103
53/167
6,502,327 B2 * 1/2003 Kume .................. B65B 55/103
34/399

(Continued)

FOREIGN PATENT DOCUMENTS

AU 2007203131 B2 7/2007
CH 511 150 A 8/1971

(Continued)

OTHER PUBLICATIONS

International Search Report (PCT/ISA/210) mailed on Nov. 13, 2012, by the European Patent Office as the International Searching Authority for International Application No. PCT/EP2012/066758.

(Continued)

*Primary Examiner* — Regina M Yoo
(74) *Attorney, Agent, or Firm* — Buchanan Ingersoll & Rooney PC

(57) ABSTRACT

There is described a unit for sterilizing a web of packaging material advanced along a given path, having, along a longitudinal portion thereof, a succession of pre-applied opening devices and adapted to be transformed in a plurality of sealed packages containing a pourable food product; the unit comprises a bath, containing a sterilizing agent in which the web with the opening devices is advanced, and an aseptic chamber connected to an outlet of the bath and housing drying mechanism for removing residual sterilizing agent from the web; the drying mechanism comprise an ejector located at a distance from the outlet of the bath and configured so as to direct a stream of air transversally to the web and onto the longitudinal portion of the web provided with the opening devices.

18 Claims, 5 Drawing Sheets

(56) References Cited

U.S. PATENT DOCUMENTS

| | | |
|---|---|---|
| 8,337,771 B2 | 12/2012 | Ferrarini et al. |
| 8,574,491 B2 | 11/2013 | Donati |
| 2002/0124526 A1 | 9/2002 | Lewis, Jr. et al. |
| 2012/0017540 A1 | 1/2012 | Tsuruta et al. |

FOREIGN PATENT DOCUMENTS

| | | |
|---|---|---|
| CN | 101316760 A | 12/2008 |
| CN | 102026877 A | 4/2011 |
| EP | 1 050 468 A1 | 11/2000 |
| EP | 1 179 479 A1 | 2/2002 |
| JP | H11-348937 A | 12/1999 |
| JP | 2002-53110 A | 2/2002 |
| JP | 2004-245545 A | 9/2004 |
| JP | 4651775 B2 | 3/2011 |
| WO | 2010/116519 A1 | 10/2010 |

OTHER PUBLICATIONS

Written Opinion (PCT/ISA/237) mailed on Nov. 13, 2012, by the European Patent Office as the International Searching Authority for International Application No. PCT/EP2012/066758.

Office Action (Text of First Office Action) issued on Sep. 28, 2014, by the State Intellectual Property Office of People's Republic of China in corresponding Chinese Patent Application No. 201280047629.0, and an English translation of the Office Action. (12 pages).

Office Action (Notice of Reasons for Rejection) issued by Japanese Patent Office on Apr. 25, 2016 in corresponding Japanese Patent Application No. 2014-532298, and an English language translation of the Office Action (7 pages).

* cited by examiner

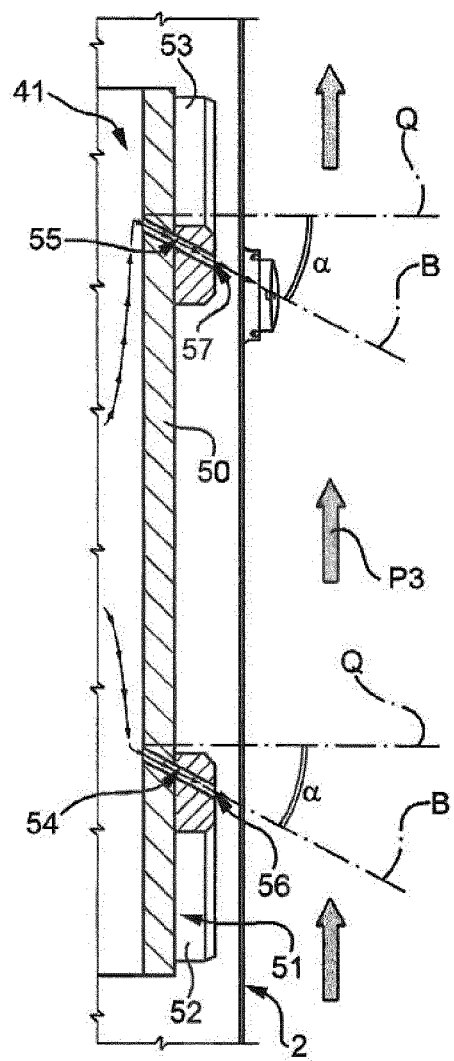
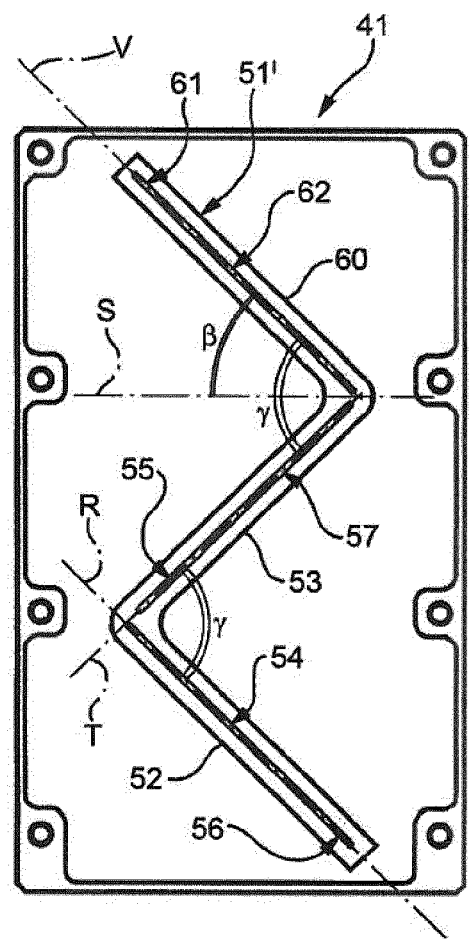
FIG. 6
FIG. 7

UNIT FOR STERILIZING A WEB OF PACKAGING MATERIAL FOR A MACHINE FOR PACKAGING POURABLE FOOD PRODUCTS

TECHNICAL FIELD

The present invention relates to a unit for sterilizing a web of packaging material for a machine for packaging pourable food products.

BACKGROUND ART

As it is known, many food products, such as fruit juice, pasteurized or UHT (ultra-high-temperature treated) milk, wine, tomato sauce, etc., are sold in packages formed from a continuous tube of packaging material made from a longitudinally sealed web.

The packaging material has a multilayer structure comprising a strong, stiff base layer, which may comprise fibrous material, such as paper, or material such as mineral-filled polypropylene. The base layer is covered on both sides with layers of heat-seal plastic material, such as polyethylene films; in the case of aseptic packages for long-storage products, such as UHT milk, the packaging material also comprises a layer of oxygen-barrier material, such as an aluminium foil or an ethyl vinyl alcohol (EVOH) foil, which is superimposed on a layer of heat-seal plastic material, and is in turn covered with another layer of heat-seal plastic material defining the inner face of the package eventually contacting the food product.

As it is known, packages of this sort are produced on fully automatic packaging machines, on which the web of packaging material is unwound off a reel and fed through a sterilizing unit, in which it is typically sterilized by immersion in a bath of liquid sterilizing agent, such as a concentrated hydrogen peroxide and water solution.

More specifically, the sterilizing unit comprises a bath filled, in use, with the sterilizing agent, into which the web is fed continuously. The bath conveniently comprises two parallel vertical branches connected at the bottom to define a U-shaped path long enough to allow sufficient time to treat the packaging material. For effective, relatively fast treatment, thus enabling a reduction in the size of the sterilizing chamber, the sterilizing agent must be maintained at a high temperature, e.g. of around 70° C.-80° C.

The sterilizing unit also defines an aseptic environment connected to the outlet of the bath, and in which the web of packaging material is dried and subsequently folded and sealed longitudinally to form a vertical tube, which is then filled continuously with the food product for packaging.

More specifically, in the aseptic environment, the web is treated to eliminate any residual sterilizing agent, the amount of which permitted in the packaged food product is governed by strict regulations (the maximum amount permitted being in the region of a fraction of one part per million).

The above treatment normally comprises a preliminary operation, whereby the drops on the packaging material are removed mechanically, and air drying.

Preliminary removal of the drops may be performed, for example, by means of a pair of squeeze rollers conveniently located close to the inlet of the aseptic environment; the packaging material is fed between the rollers and comes out still covered with a film of sterilizing agent, but with no macroscopic drops.

Drying may be performed using air knives directed onto the opposite faces of the web of packaging material, supplied with sterile air, and for evaporating any leftover traces of sterilizing agent.

Before leaving the aseptic environment, the web is folded into a cylinder and sealed longitudinally to form a continuous vertical tube in known manner. The tube of packaging material, in effect, forms an extension of the aseptic environment, and is filled continuously with the pourable food product, and then fed to a (transverse) form-and-seal unit for forming the individual packages, and in which the tube is gripped and sealed between pairs of jaws to form pillow packs.

The pillow packs are separated by cutting the sealed portions between the packs, and are then fed to a final folding station where they are folded mechanically into the finished form.

In some known solutions, the packages coming out of the form-and-seal unit are already provided with reclosable opening devices. In these cases, the opening devices are pre-applied, e.g. injection molded directly, to the web of packaging material before the latter is supplied to the sterilizing unit.

Packaging machines of the type described above are used widely and satisfactorily in a wide range of food industries to produce sealed packages from a web of packaging material. Performance of the sterilizing units of such machines, in particular, ensures ample compliance with regulations governing sterility of the packages and the amount of residual sterilizing agent in the finished packages.

Within the industry, however, a demand for further improvements is felt, particularly in view of the continual increase in the output rate of the packaging machines and of the impact that such increase may have on the solutions based on the application of the opening devices to the packaging material before the latter is fed to the sterilizing unit.

As a matter of fact, continually increasing the output rate obviously reduces the time available to remove all the residual sterilizing agent from each portion of the web of packaging material travelling through the aseptic environment, and especially on the pre-applied opening devices, which, having a more complex geometry than the web, tend to form some sorts of traps for the residual sterilizing agent.

DISCLOSURE OF INVENTION

It is an object of the present invention to provide a unit for sterilizing a web of packaging material with pre-applied opening devices, designed, even alongside drastic increases in output rate, to ensure ample compliance with regulations governing the permissible amount of residual sterilizing agent on the finished packages.

According to the present invention, there is provided a unit for sterilizing a web of packaging material, as claimed in claim 1.

BRIEF DESCRIPTION OF THE DRAWINGS

A preferred, non-limiting embodiment of the present invention will be described by way of example with reference to the accompanying drawings, in which:

FIG. 6 shows a larger-scale detail of FIG. 3 sterilizing unit; and

FIG. 7 shows a front view of a possible variant of the FIG. 5 nozzle.

BEST MODE FOR CARRYING OUT THE INVENTION

Figure 1:
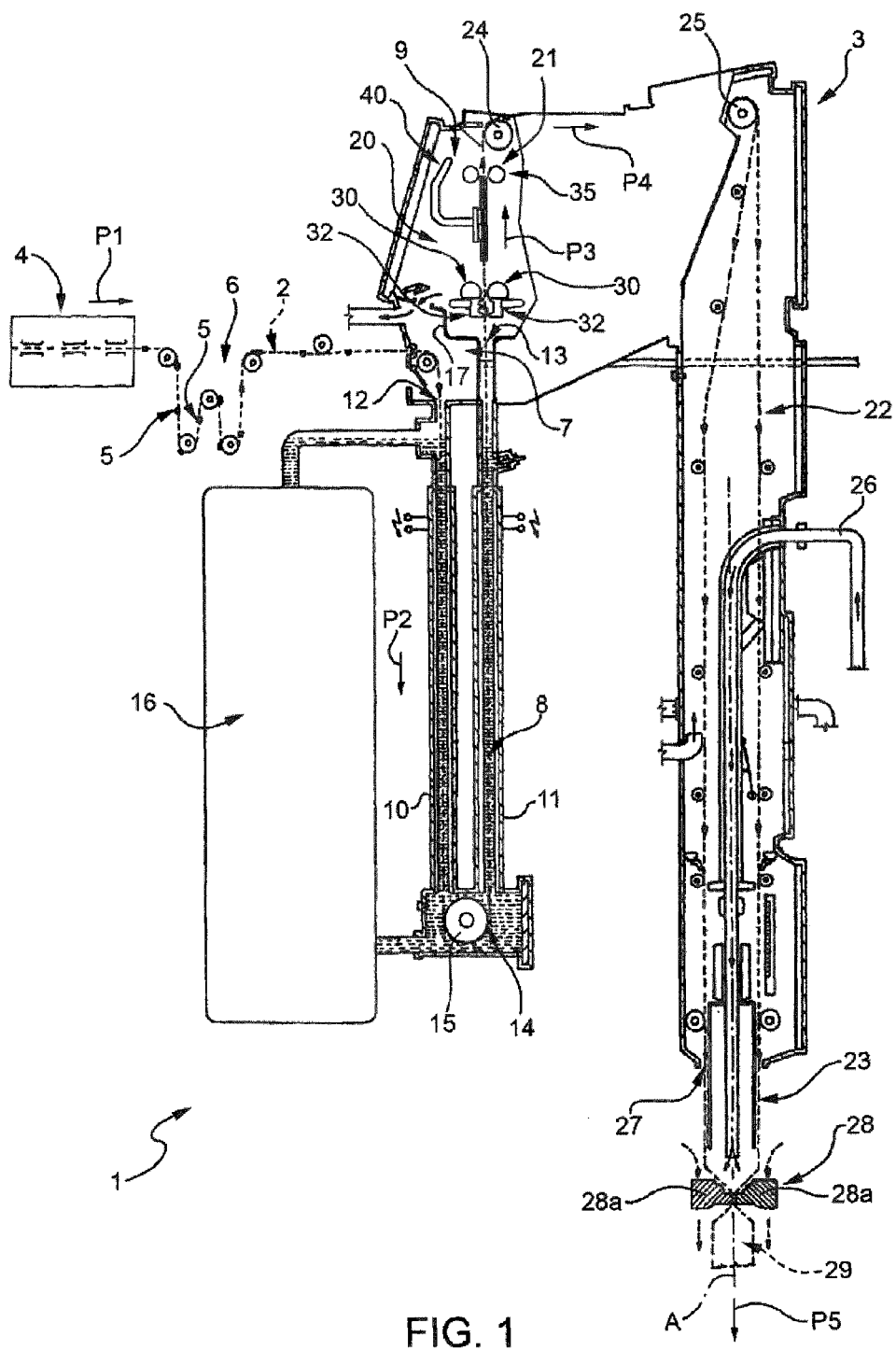
FIG. 1 shows a diagram of a machine for packaging pourable food products from a web of packaging material and featuring a sterilizing unit in accordance with the teachings of the present invention.

Number 1 in FIG. 1 indicates as a whole a packaging machine for continuously producing aseptic sealed packages of a pourable food product from a web of packaging material 2 (hereafter referred to simply as "web 2").

Machine 1 comprises a sterilizing unit 3, to which web 2 is fed off a reel (not shown) along a path P1.

Machine 1 also comprises an application unit 4 for applying reclosable opening devices 5 to web 2 and located upstream from the sterilizing unit 3 along path P1. Application unit 4 is conveniently defined by a known station for injection molding plastic material, and through which web 2 is fed in steps. At the output of application unit 4, the web 2 is provided, along an intermediate longitudinal portion 2a thereof (see FIGS. 2 and 4), with a succession of equally spaced opening devices 5 (only schematically shown in FIGS. 1 and 3 along limited portions of the web 2; see also FIGS. 2, 4 and 6 for more detailed views of opening devices 5). At the output of application unit 4 and upstream from sterilizing unit 3, a web store 6 is conveniently provided to compensate for the different web feeds of the two units (step feed and continuous feed respectively).

Sterilizing unit 3 basically comprises a transition chamber 7, into which web 2 is first fed, a sterilizing bath 8 containing a liquid sterilizing agent, e.g. a 30% solution of hydrogen peroxide ($H_2O_2$) and water, through which web 2 is advanced, and an aseptic chamber 9, in which web 2 is dried, as explained in detail below.

Bath 8 is substantially defined by a U-shaped conduit filled, in use, with sterilizing agent to a predetermined level. The U-shaped conduit is defined by two vertical, respectively inlet and outlet, branches 10, 11 having respective top openings 12, 13, which respectively define the inlet and outlet of web 2 into and out of bath 8, and communicate respectively with transition chamber 7 and aseptic chamber 9; the two branches 10, 11 are connected at the bottom by a bottom portion 14 of bath 8 housing a horizontal-axis guide roller 15.

Inside bath 8, web 2 therefore describes a U-shaped path P2 of such a length as to keep the packaging material long enough inside the sterilizing agent.

Bath 8 is connected to a peroxide control circuit 16—known and therefore not shown in detail—and is maintained, in use, at a controlled temperature, e.g. of around 70° C.-80° C.

Aseptic chamber 9 is located above transition chamber 7, is separated from it by a partition 17 and has an inlet for web 2, coincident with the outlet (top opening 13) of bath 8.

Aseptic chamber 9 comprises a top portion 20, housing drying means 21 for removing residual sterilizing agent from web 2 and opening devices 5, and a bottom portion or tower 22 extending vertically and parallel to bath 8, and in which web 2 is folded longitudinally into a cylinder and sealed longitudinally to form a continuous cylindrical tube 23 having a vertical axis A.

Aseptic chamber 9 is maintained slightly above ambient pressure, so that any leakage through the seals occurs outwards as opposed to inwards of the chamber.

As visible in FIG. 1, inside top portion 20 of aseptic chamber 9, web 2 describes first a vertical path P3 extending on the prolongation of the vertical portion of path P2 in outlet branch 11 and is then diverted by respective rollers 24, 25 onto a substantially horizontal path P4 and onto a vertical path P5 in the tower 22, parallel to axis A of the tube 23.

In known manner and not described in detail, tube 23, formed downstream from roller 25, is filled continuously with the product for packaging by means of a fill conduit 26, and comes out downwards through a bottom opening 27 in aseptic chamber 9, of which it substantially forms an extension.

Machine 1 comprises a known transverse form-and-seal unit 28, not shown in detail, in which tube 23 of packaging material is gripped between pairs of jaws 28a, which seal tube 23 transversely to form aseptic pillow packs 29 eventually formed by known cutting and folding operations into individual packages.

With reference to FIGS. 1 to 4, drying means 21 comprise two idle squeeze rollers 30 having parallel horizontal axes, located close to the inlet of aseptic chamber 9, on opposite sides of web 2, and at least one of which is covered with relatively soft material. Squeeze rollers 30 exert pressure on respective opposite faces of web 2 to squeeze the drops of sterilizing agent out and back into bath 8.

Squeeze rollers 30 (FIGS. 2 and 4) conveniently comprise respective intermediate recesses 31 located at intermediate longitudinal portion 2a of web 2 to permit the passage of opening devices 5 without interfering with the rollers 30. In the example shown, recesses 31 are defined by respective smaller-diameter intermediate portions of squeeze rollers 30.

Figure 3:
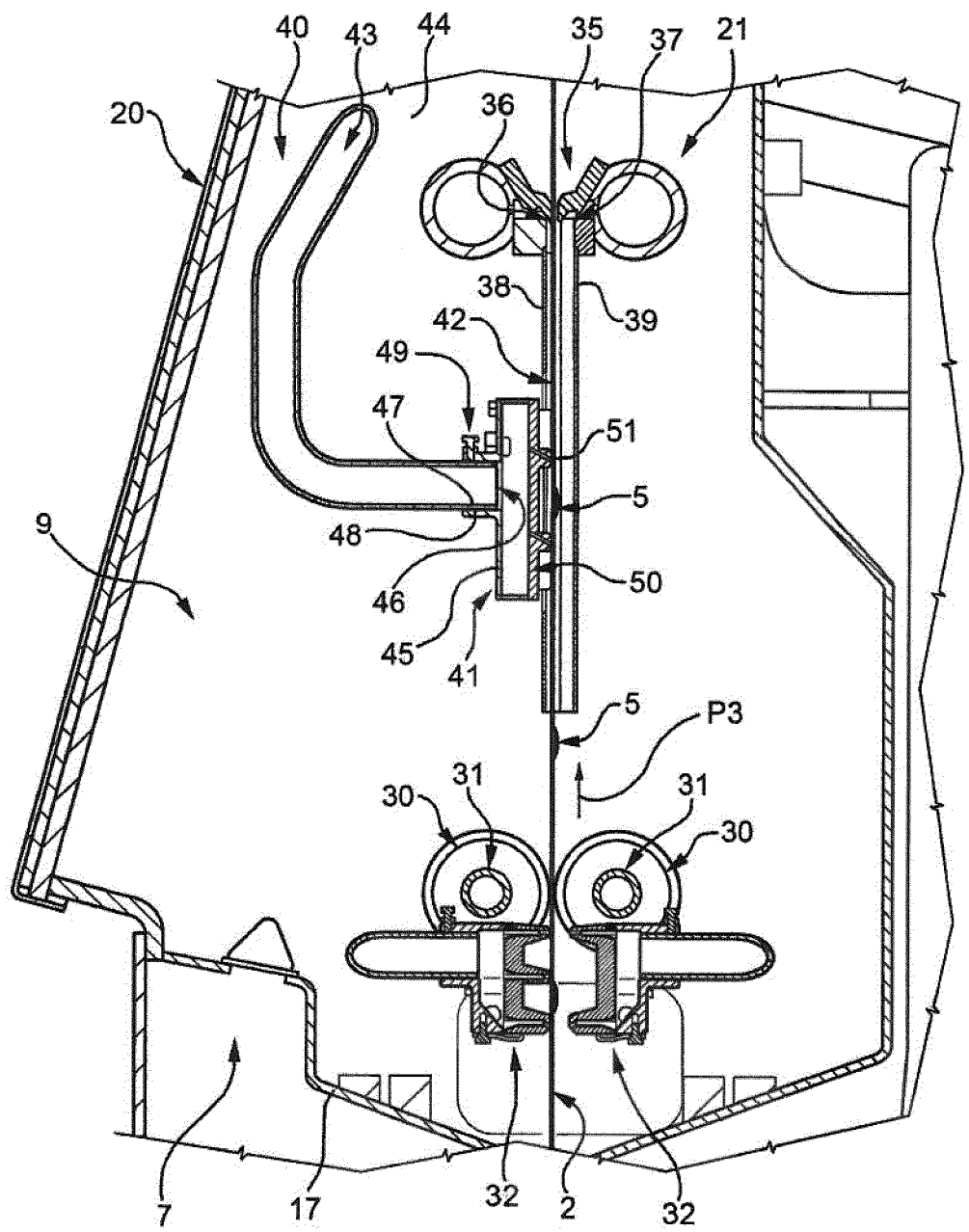
FIG. 3 shows a vertical section of the part of the sterilizing unit of FIG. 2.
Figure 4:
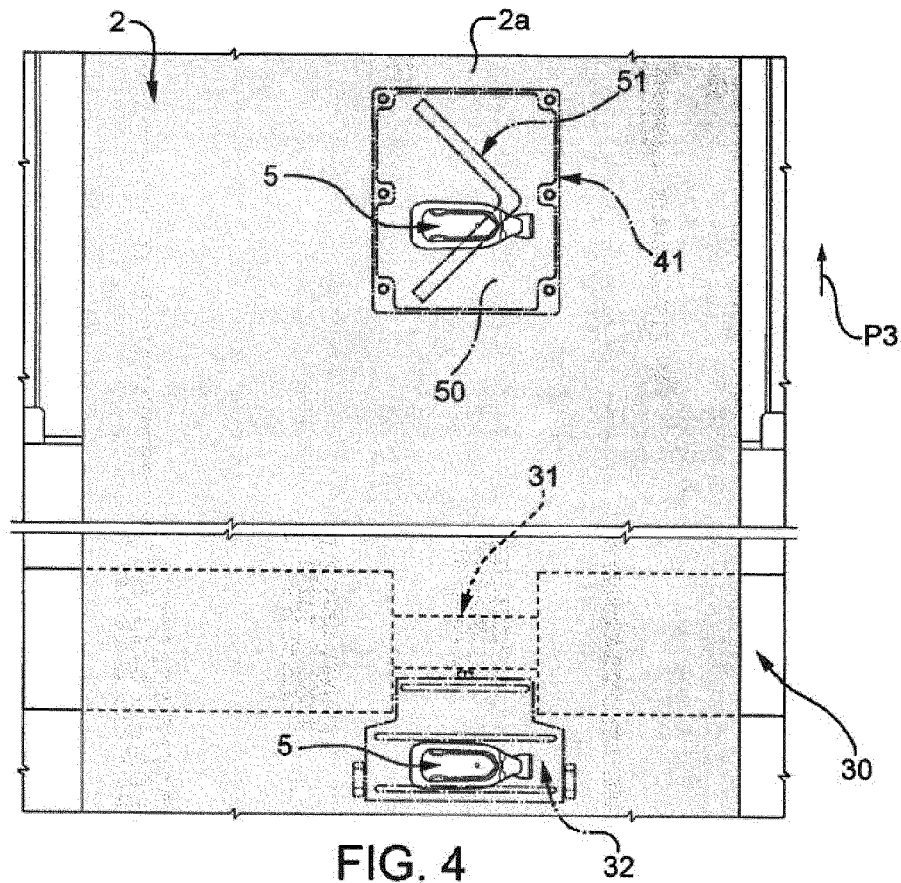
FIG. 4 shows a portion of the web of packaging material of FIG. 1 when advancing through the part of the sterilizing unit of FIG. 2.

As visible in FIGS. 1, 3 and 4, drying means 21 also comprise, in a known manner, two nozzles 32 located at the inlet of aseptic chamber 9, on opposite sides of web 2, immediately upstream from squeeze rollers 30 along path P3 and at recesses 31 of the rollers 30.

Nozzles 32 provide for directing respective streams of air onto intermediate longitudinal portion 2a of web 2, at opening devices 5, to remove residual sterilizing agent from the opening devices 5. In particular, nozzles 32 are configured so as to push the residual sterilizing agent away from the opening devices 5 and towards the opposite sides of the web 2 and the bath 8.

Figure 2:
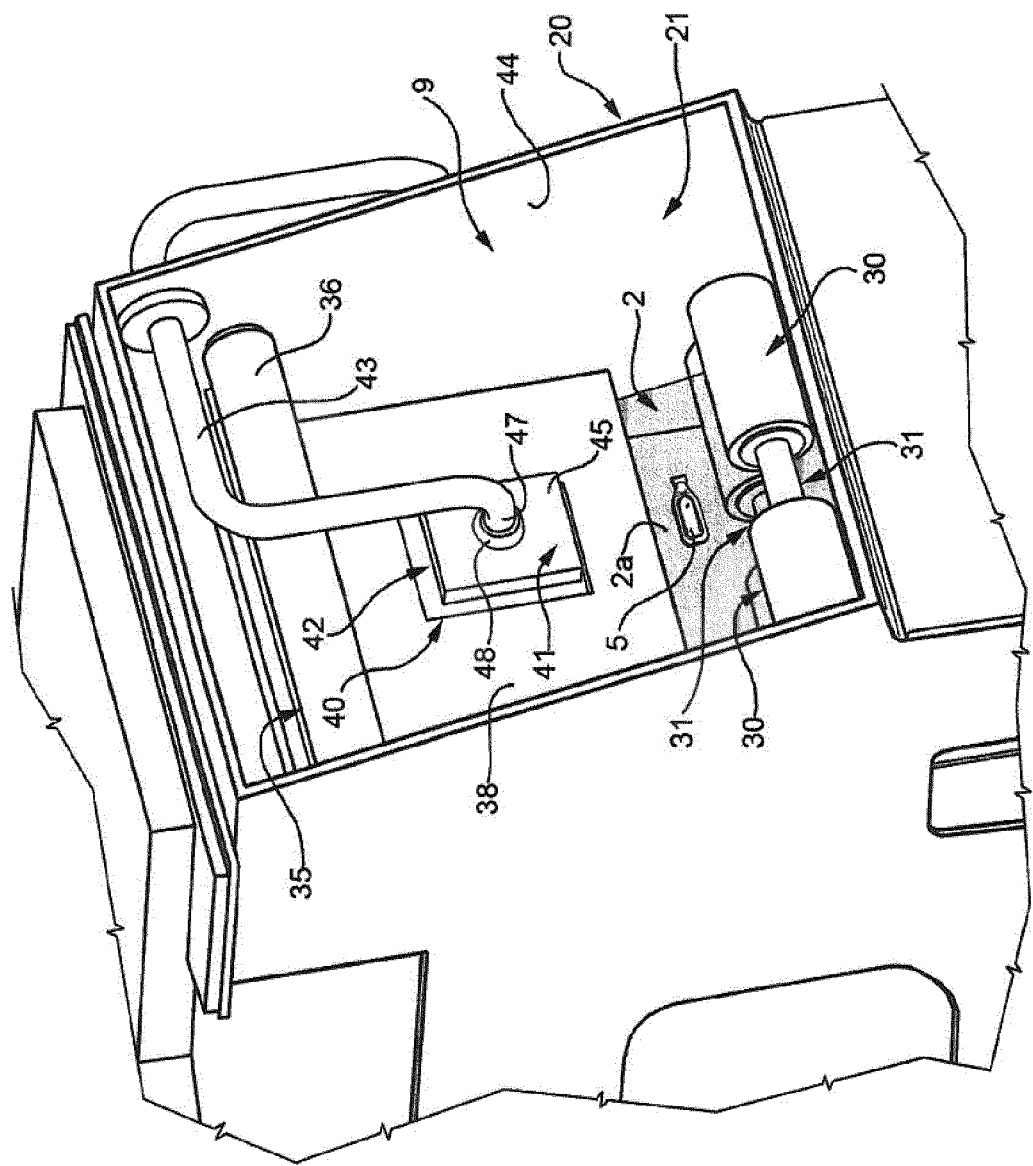
FIG. 2 shows a larger-scale view in perspective of part of the FIG. 1 sterilizing unit.

As shown in FIGS. 1 to 3, drying means 21 also comprise two so-called "air knives" 35 located on opposite sides of web 2, downstream from squeeze rollers with reference to path P3 and therefore over such rollers 30.

Each air knife 35 comprises a relative nozzle 36, 37 for directing a stream of air downwards (i.e. towards bath 8) and on a relative face of web 2 and, and a relative guide wall 38, 39 arranged parallel to web 2 and at reduced distance therefrom so as to guide the relative stream of air, in use, in a direction substantially parallel to the web 2 but opposite to the travelling direction thereof.

As visible in FIG. 3, guide wall 38 is located facing the surfaces of opening devices 5 designed to be oriented towards the inside of the finished packages and having a concave configuration; guide wall 39 is therefore located facing the opposite surfaces of the opening devices 5, which have a convex configuration.

With reference to FIGS. 1 to 4, drying means 21 further comprise additional ejecting means 40 arranged at a given distance from the outlet of bath 8 and configured so as to direct a stream of air transversally to web 2 and onto the longitudinal portion 2a of the web 2 provided with the opening devices 5.

Advantageously, ejecting means 40 are located on guide wall 38 and downstream from squeeze rollers 30 along path P3 of web 2.

The Applicant has observed that this location permits to increase the drying effect on opening devices 5 after the most part of residual sterilizing agent has been removed by squeeze rollers 30. In particular, the zone immediately adjacent to the squeeze rollers 30 is characterized by a certain level of turbulence due to presence of drops of sterilizing agent; by positioning the additional ejecting means 40 at a given distance from that turbulent zone, and in particular on the air knives 35, permits to obtain an additional drying step on the opening devices 5 without increasing the turbulence at the squeeze rollers 30.

With reference to FIGS. 2 to 6, ejecting means 40 comprise a nozzle 41 housed with play within a window 42 of guide wall 38 so as to face web 2, and a supply conduit 43 extending inside aseptic chamber 9 from a side wall 44 thereof and carrying, in a projecting manner, nozzle 41.

In particular, nozzle 41 comprises a hollow box-shaped body 45 having a rear opening 46 connected to one end 47 of supply conduit 43; more specifically, rear opening 46 is delimited by a projecting edge 48 engaged by end 47 of supply conduit 43 and secured thereto by releasable fastening means 49, such as screws.

Body 45 is closed at the front by a plate 50 provided with a hollow shaped front projection 51 communicating with the cavity of the body 45 and adapted to direct a stream of air onto web 2.

In the example shown in the accompanying drawings, plate 50 has a rectangular profile and projection 51 is substantially L-shaped with two branches 52, 53 parallel to web 2 and extending in an inclined manner with respect to the travelling direction thereof at the zone of nozzle 41.

Each branch 52, 53 is provided with a relative outlet port 54, 55, which is preferably defined by a relative slot having substantially the same extension as the relative branch 52, 53.

Outlet ports 54, 55 are so configured to direct the stream of air in an inclined direction towards bath 8. More specifically (see in particular FIG. 6), each outlet port 54, 55 has a relative axis B transversal to web 2 and inclined towards bath 8; as indicated in FIG. 6, the axis B of each outlet port 54, 55 forms an acute angle $\alpha$, different from zero, with a direction Q orthogonal to the web 2.

Figure 5:
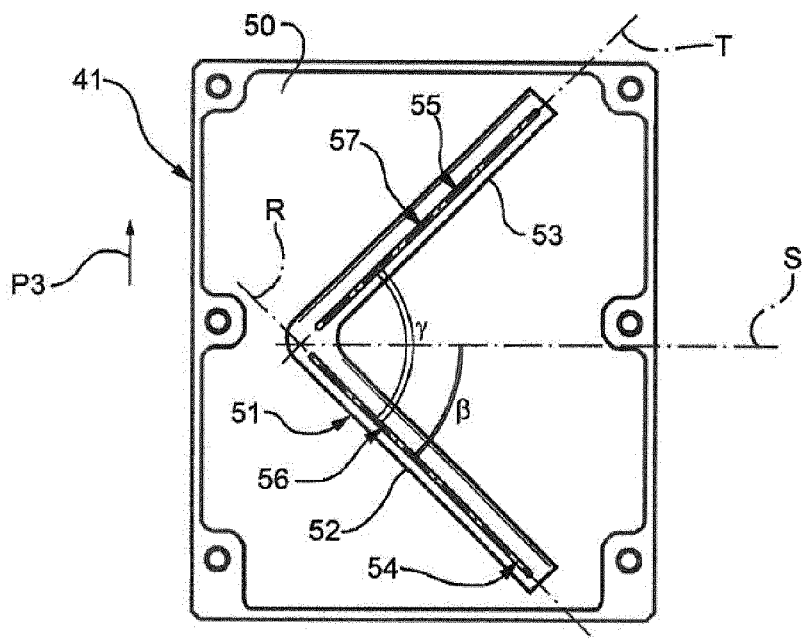
FIG. 5 shows a larger-scale front view of a nozzle of the sterilizing unit of FIGS. 1 to 3.

With particular reference to FIG. 5, outlet port 54, which is located upstream of outlet port 55 along path P3, defines a relative outlet area 56, from which the stream of air is issued in use and which extends along a direction R parallel to web 2 and forming an acute angle $\beta$, different from zero, with a horizontal direction S parallel to the web 2 and orthogonal to the travelling direction of the web 2 at the zone of nozzle 41.

In an analogous manner, outlet port 55 defines a relative outlet area 57, from which the stream of air is issued in use and which extends along a direction T parallel to web 2 and transversal to direction R and to the travelling direction of the web 2 at the zone of nozzle 41.

In the example shown, outlet areas 56, 57 have opposite inclinations with respect to the travelling direction of the web 2 at the zone of nozzle 41.

Moreover, as visible in FIG. 5, direction T forms an angle $\gamma$ of 90° with direction R. In this way, the stream of air issued from outlet area 57 does not interfere with the stream of air issued from outlet area 56.

In actual use, web 2 is fed in steps through application unit 4 where opening devices 5 are formed, and continuously through bath 8 and aseptic chamber 9.

On entering aseptic chamber 9, longitudinal portion 2a of web 2 with pre-applied opening devices 5 is swept on both faces by the air streams from nozzles 32; such air streams push the residual sterilizing agent away from the opening devices 5 and towards the opposite sides of the web 2 and the bath 8.

Web 2 is then fed through squeeze rollers 30, which squeeze the drops of residual sterilizing agent out and back into bath 8.

At this point, web 2 enters the air knives 35 and is swept by sterile-air streams ejected from nozzles 36, 37 and guided along the opposite faces of the web 2 by guide walls 38, 39.

During the passage through guide walls 38, 39, the longitudinal portion 2a of web 2 with opening devices 5 is also swept by the stream of air ejected by nozzle 41.

Due to the opposite inclined configurations of outlet areas 56, 57 of ports 54, 55, each opening device 5 is first dried from a first side end to a second side end opposite to the first side end and, then, from this latter side end to the first one. In this manner, the jet of air issued from the downstream outlet port 55 does not interfere with the jet of air issued from the upstream outlet port 54, so as to make the removal action of the residual sterilizing agent from opening devices 5 very effective, even with increased output rates of the packaging machine 1.

Once left the air knives 35, the web 2 is diverted by roller 24 along path P4 and by roller 25 along path P5.

Web 2 is then folded into a cylinder and sealed longitudinally to form tube 23, which is filled continuously with the pourable food product from conduit 26, and is gripped and sealed transversely by jaws 28a to form a succession of pillow packs 29.

The variant of FIG. 7 relates to a different configuration of nozzle 41, whose front projection, indicated as a whole with 51', differs from corresponding projection 51 in that it comprises an additional branch located downstream of branch 53 along path P3 and extending parallel to branch 52.

More specifically, the additional branch 60 is provided with a relative outlet port 61 in the form of a slot defining a relative outlet area 62 of the same type as outlet areas 56, 57 and which extends along a direction V parallel to web 2 and to direction R, and therefore forming an angle $\gamma$ of 90° with direction T.

According to a possible alternative not shown, the front projection 51 of nozzle 41 may be also formed by a succession of alternating branches 52, 53 defining respective outlet areas 56, 57, each having an opposite inclination with respect to the adjacent one.

According to another possible alternative not shown, the front projection 51 of nozzle 41 may be also formed by a single branch 52, 53 or 60 provided with a relative outlet port 54, 55 or 61 defining a single outlet area 56, 57 or 62.

According to a further possible alternative not shown, each outlet port 54, 55, 60 may be also defined by a row of holes, all together forming the relative outlet area 56, 57, 62.

Tests have been carried out on further different configurations of the outlet areas of nozzle 41, and namely:
  a first configuration defined by a succession of horizontal outlet areas, i.e. extending parallel to direction S; and
  a second configuration defined by a succession of parallel and inclined outlet areas, i.e. extending parallel to direction R or direction T.

These tests have revealed that the above-indicated configurations are less effective than the preferred ones of FIGS. 5 and 7. As a matter of fact, in both the tested solutions, the upstream jet of air tends to disturb, or better "to raise", the immediately downstream jet and so on, with the result that the opening devices 5 are not well scavenged by the impinging flow of air.

The advantages of sterilizing unit 3 according to the present invention will be clear from the foregoing description.

In particular, thanks to the location of nozzle 41 on guide wall 38 of air knives 35 at a distance from squeeze rollers 30 and to the particular configuration of outlet ports 54, 55, 60, which are inclined towards bath 8 and have respective outlet areas 56, 57, 62 parallel to web 2 but inclined with respect to the web travelling direction, a very effective current of air can be directed onto the opening devices 5 arranged on the longitudinal portion 2a of web 2. In this way, the opening devices 5 are scavenged both in the web travelling direction and laterally with respect to this latter direction.

Moreover, due to the fact that the extension direction T, V of each outlet area 57, 62 is orthogonal to the extension direction R, T of the immediately adjacent upstream outlet area 56, 57, the streams of air issued from the different outlet areas 56, 57, 62 do not interfere with one another.

Even alongside drastic increases in packaging machine output rates, therefore, sterilizing unit 3 safely ensures ample compliance with current regulations governing the permissible amount of residual sterilizing agent on the packaging material and opening devices 5 of the finished packages.

Clearly, changes may be made to sterilizing unit 3 as described and illustrated herein without, however, departing from the scope defined in the accompanying claims.

The invention claimed is:

1. A unit for sterilizing a web of packaging material advanced along a given path, having, along a longitudinal portion thereof, a succession of pre-applied opening devices and adapted to be transformed in a plurality of sealed packages containing a pourable food product, said unit comprising
a bath containing a sterilizing agent in which said web with said opening devices is advanced, said bath possessing an outlet;
an aseptic chamber connected to said outlet of said bath and housing drying means for removing residual sterilizing agent from said web;
wherein said drying means comprise:
ejecting means located at a distance from said outlet of said bath and configured so as to direct a stream of air transversally to said web and onto the longitudinal portion of said web provided with said opening devices; and
two air knives located on opposite sides of said web when said web is advanced along the given path, wherein each of said two air knives comprises a nozzle for directing a stream of air on one of two faces of said web, and a guide wall for guiding said stream of air, in use, in a direction opposite to a travelling direction of said web; and wherein said ejecting means are arranged on one of said guide walls.

2. The unit as claimed in claim 1, wherein said one of said guide walls is located facing surfaces of said opening devices designed to be oriented towards the inside of the sealed packages.

3. The unit as claimed in claim 1, wherein said drying means comprise two squeeze rollers cooperating with opposite faces of said web and having respective recesses at said longitudinal portion of said web to permit passage of said opening devices, and wherein said ejecting means are arranged downstream from said squeeze rollers along said given path of said web.

4. The unit as claimed in claim 3, wherein said drying means comprise further ejecting means for directing air onto said longitudinal portion of said web and arranged close to said outlet of said bath and immediately upstream from said squeeze rollers.

5. The unit as claimed in claim 1, wherein said ejecting means comprise at least a first outlet area, which is elongated along a first direction parallel to said web, the first outlet area configured to outlet the stream of air in a direction transverse to the travelling direction of the web at a zone of said ejecting means.

6. The unit as claimed in claim 5, wherein said first direction forms an acute angle, different from zero, with a second direction, wherein the second direction is parallel to the web and orthogonal to the travelling direction of the web at the zone of said ejecting means.

7. The unit as claimed in claim 5, wherein said ejecting means comprise a second outlet area of a same type as the first outlet area, the second outlet area being elongated along a fourth direction parallel to said web and transversal to the first direction and to the travelling direction of the web at the zone of said ejecting means.

8. The unit as claimed in claim 7, wherein said first and second outlet areas have opposite inclinations with respect to the travelling direction of the web.

9. The unit as claimed in claim 7, wherein the stream of air issued from said second outlet area does not interfere with the stream of air issued from said first outlet area.

10. The unit as claimed in claim 7, wherein said fourth direction forms an angle of 90° with said first direction.

11. The unit as claimed in claim 7, wherein said ejecting means comprise a third outlet area of the same type as said first and second outlet areas, said third outlet area being elongated along a fifth direction parallel to said web and to said first direction; said third outlet area being arranged downstream from said second outlet area along said given path of said web.

12. The unit as claimed in claim 1, wherein said ejecting means are configured to direct said stream of air in an inclined direction towards said bath.

13. The unit as claimed in claim 12, wherein said ejecting means comprise at least a first outlet port inclined towards said bath.

14. The unit as claimed in claim 13, wherein said first outlet port forms an acute angle, different from zero, with a third direction orthogonal to the web.

15. The unit as claimed in claim 13, wherein said first outlet port is a slot defining a first outlet area.

16. The unit as claimed in claim 1, wherein the guide wall of each of the two air knives is movable.

17. A unit for sterilizing a web of packaging material advanced along a given path, the web of packaging material configured to be transformed into a plurality of sealed packages containing a pourable food product and the web of packaging material possessing a succession of pre-applied opening devices along a longitudinal portion of the web, the unit comprising:
a bath configured to contain a sterilizing agent, the web with the opening devices passing through the bath as the web advances along the given path, the bath possessing an outlet;
an aseptic chamber connected to the outlet of the bath;
drying means for removing residual sterilizing agent from the web, the drying means being housed in the aseptic chamber, the drying means comprising ejecting means located at a distance from the outlet of the bath and configured to direct first and second streams of air transversally to the web onto the longitudinal portion of the web provided with the opening devices;

the ejecting means comprising a first outlet area elongated along a first direction parallel to the web and configured to direct the first stream of air in a direction transverse to a travelling direction of the web; and the ejecting means comprising a second outlet area elongated along a second direction parallel to the web and transverse to the first direction, the second outlet area configured to direct the second stream of air in a direction transverse to the travelling direction of the web.

18. A unit for sterilizing a web of packaging material advanced along a given path, the web of packaging material possessing a first face and a second face opposite of the first face, the web configured to be transformed into a plurality of sealed packages containing a pourable food product and the web of packaging material possessing a succession of pre-applied opening devices along a longitudinal portion of the web, the unit comprising:

a bath configured to contain a sterilizing agent, the web with the opening devices passing through the bath when the web advances along the given path, the bath possessing an outlet;

an aseptic chamber connected to the outlet of the bath;

a squeeze roller configured to remove residual sterilizing agent from the web moving in a travelling direction, the squeeze roller being housed in the aseptic chamber;

an air nozzle configured to remove residual sterilizing agent from the web, the air nozzle being located at a distance from the outlet of the bath and configured to direct a stream of air transversally to the web onto the longitudinal portion of the web;

a first air knife housed in the aseptic chamber, the first air knife comprising a first nozzle that directs a stream of air on the first face of the web, and a first guide wall that guides the stream of air, in use, in a direction opposite to the travelling direction of said web;

a second air knife housed in the aseptic chamber and positioned on an opposite side of the web from the first air knife when the web is advanced along the given path, the second air knife comprising a second nozzle that directs a second stream of air on the second face of the web, and a second guide wall that guides the second stream of air, in use, in a direction opposite to the travelling direction of said web; and the air nozzle being mounted on one of the first guide wall and the second guide wall.

\* \* \* \* \*